United States Patent [19]

Meloul et al.

[11] Patent Number: 5,330,480
[45] Date of Patent: Jul. 19, 1994

[54] SURGICAL DRILL

[75] Inventors: Raphael F. Meloul, Randolph; Jose F. Lizardi, Medfield, both of Mass.

[73] Assignee: Codman & Shurtleff, Inc., Randolph, Mass.

[21] Appl. No.: 25,977

[22] Filed: Mar. 3, 1993

[51] Int. Cl.⁵ .............................................. A61B 17/00
[52] U.S. Cl. ..................................... 606/80; 606/170; 606/173
[58] Field of Search .................... 606/53, 79, 80, 86, 606/167, 170, 172, 173, 180

[56]         References Cited
         U.S. PATENT DOCUMENTS

| | | | |
|---|---|---|---|
| 2,842,131 | 7/1958 | Smith | 606/173 |
| 3,797,497 | 3/1974 | Crim et al. | 606/173 |
| 4,362,161 | 2/1982 | Reimels et al. | |
| 4,391,557 | 3/1982 | Bofinger et al. | |
| 4,699,550 | 10/1987 | Baker | |
| 4,884,571 | 12/1989 | Baker | |

OTHER PUBLICATIONS

Acra Cut® Product Brochure by Acra-Cut, Inc. of Acton, Mass., Copyright Date 1991.

Primary Examiner—Stephen C. Pellegrino
Attorney, Agent, or Firm—Lahive & Cockfield

[57] ABSTRACT

A surgical drill assembly is provided having a clutch mechanism that requires a sufficient axial load on cutting surfaces of the drill to enable rotation of the drill. Rotation of the drill ceases almost immediately upon the axial load falling below the predetermined axial load threshold. In one embodiment the drill assembly is disposable, and is virtually impossible to disassemble and reassemble to an operative form. In another embodiment the drill assembly is reusable. The reusable embodiment includes a drill body that enables quick and easy attachment and detachment of a drill head. The reusable drill body is of a unitary construction that can be sterilized and reused without any disassembly.

13 Claims, 7 Drawing Sheets

SURGICAL DRILL

BACKGROUND OF THE INVENTION

The invention relates to surgical drill assemblies useful for penetrating bone.

Many surgical techniques require the perforation or drilling of bone. Cranial surgery, in particular, requires control over the cutting depth of a drill so that drilling takes place only through bone and not through the delicate dura underlying the bone. During surgery that requires penetration of the skull it is critical that drill rotation cease once the skull is effectively perforated, and before any damage is done to underlying dura.

There exist cranial perforators that permit drill bit rotation only when the drill bit is subjected to an axial load of a desired magnitude. Once the load is removed, or falls below a predetermined threshold, rotation of the drill ceases. Such devices that utilize a clutch mechanism which enables a driver to be engaged only upon sufficient axial load are disclosed in U.S. Pat. Nos. 2,842,131; 4,362,161; 4,319,577; 4,884,571; and 4,699,550.

Many existing surgical drill constructions utilize reusable drill bits and drill assemblies. After use, it is necessary to disassemble the drill, sterilize the drill components, and reassemble the drill before a subsequent use. Disassembly and reassembly is undesirable because it is time consuming, labor intensive, and because there always exists the possibility that reassembly will not be performed correctly. Improper reassembly of such a drill can lead to drill failure and consequently to patient injury or death. There is thus a need for economical and effective disposable surgical drill assemblies. It would also be advantageous to provide reusable surgical drill assemblies that can be rapidly and effectively disassembled and reassembled.

It is thus an object of the invention to provide a construction for a bone drill assembly that efficiently and effectively disables drill bit rotation when the drill bit is no longer subjected to a sufficient axial load. A further object is to provide such a drill assembly that is disposable. Another object is to provide a reusable drill that is easily disassembled and reassembled. It is also an object to provide a reusable drill that does not require disassembly of components before serialization. These and other objects, features and advantages of the present invention will become more apparent from the following description.

SUMMARY OF THE INVENTION

The present invention provides a drill assembly useful to penetrate bone without penetrating any soft tissue underlying the bone. The drill assembly of the present invention is well adapted for use as a cranial drill, though it is also useful in perforating bone structures in other parts of the body.

In general terms, the drill assembly has two distinct parts: a drill head and a drill body. The drill head comprises a primary drill member housed within a central axial bore formed within a cylindrical secondary drill member. Both the primary and secondary drill members have cutting surfaces at their distal ends and elongate stems at their proximal ends. The elongate stem of the primary drill member extends beyond the proximal end of the secondary drill member and features one or more driver engaging surfaces. The primary and secondary drill members are secured to each other by a coupling mechanism that enables rotation of the secondary drill member upon rotation of the primary drill member.

In one aspect of the invention, the drill body and drill head are constructed to form a disposable unit that is incapable of being disassembled and reassembled.

The drill body of the disposable unit comprises a housing member having an axial bore at its distal end which is adapted to receive the elongate stems of the primary and secondary drill members. In this embodiment, proximal portions of the drill members are disposed within the housing such that disassembly without damage to the device is virtually impossible. Preferably, a device such as an annular bearing is adapted to fit around the proximal portions of the primary and secondary drill members while allowing free rotation of the drill members. The bearing, in turn, preferably is adapted to be disposed within the housing in an interference fit such that independent rotation of the drill head and body is facilitated.

The drill assembly also includes a clutch mechanism that enables drill member rotation when the primary drill member is subjected to a sufficient axial load, and which prevents rotation when the load falls below a predetermined threshold. The clutch mechanism preferably is disposed at a bottom portion of the housing. The clutch can include a driver and a compression means for biasing the driver engaging surfaces on the proximal end of the primary drill member away from the driver. The driver preferably has substantially vertical drive surfaces that contact the driver engaging surfaces when an axial load overcomes the biasing forces to facilitate only clockwise rotation of the drill members.

In another embodiment, the drill assembly is constructed so as to be reusable. In this embodiment, the drill head can be as described above, and can be disposed of after use, or it can be sterilized and reused. The drill head is easily and conveniently mounted in and removed from a socket disposed in the drill body. The drill body, which includes the socket, is of a unitary construction and need not be disassembled, and may be sterilized and reused following a surgical procedure.

The reusable drill body preferably comprises a housing member having a cylindrical socket for receiving the elongate stems of the drill members. The socket is defined by an inner sleeve which has a radially displaceable engagement bearing protruding through an aperture at its distal end. A retractable outer sleeve is slidably disposed over the inner sleeve for forcing the bearing into the socket when in a non-retracted position. The two sleeves are also sealed to prevent contamination of interior regions of the drill body.

The bearing is adapted to engage an annular groove on an external surface of the stem of the secondary drill member when the outer sleeve is in a forward, or non-retracted position and the bearing extends into the interior or the housing. This engagement thus allows the drill head to be secured within the drill housing when the outer sleeve is in the forward non-retracted position. Retracting the outer sleeve relieves the inward force on the engagement bearing to enable the groove on the secondary drill member to be disengaged from the bearing to enable easy removal of the drill head. Despite the engagement by bearing and groove, the drill head is still able to rotate independently of the drill body when the driver is not engaged.

The reusable drill assembly also includes a clutch mechanism, preferably disposed within the housing, that enables rotation of the drill members only if there is an axial load on the primary drill member that exceeds a predetermined threshold. Preferably, the clutch is constructed to allow the drill head to rotate only in the clockwise direction. This clutch mechanism can be similar to that used with a disposable drill assembly, but preferably is of a more durable construction so as to provide a longer useful lifetime.

BRIEF DESCRIPTION OF THE DRAWINGS

The foregoing and other objects of the invention, the various features thereof, as well as the invention itself, may be more fully understood from the following description, when read together with the accompanying drawings.

DETAILED DESCRIPTION OF THE DRAWINGS

The drill assembly of the invention is useful for penetrating bone in a controlled manner such that drill rotation is not possible absent a sufficient axial load on the drill. Such a drill construction is necessary for many surgical techniques, such as cranial surgery, where soft, delicate tissue underlies the bone structure to be penetrated. Once the bone structure is penetrated, the axial load upon the drill will significantly decrease and drill rotation will cease almost immediately.

In one embodiment of the invention, the drill assembly is entirely disposable, thus eliminating the time-consuming disassembly and reassembly of the drill. In another embodiment, the drill assembly is reusable and is constructed such that attachment of drill heads to the drill body can be accomplished quickly, easily, and without error. The reusable drill assembly of the invention is also easily sterilizable.

FIGS. 1 through 6 illustrate a drill assembly, and its various components, intended to be entirely disposable.

As illustrated in FIGS. 1 through 4, disposable drill assembly 10 comprises at its distal end, a drill head 12 formed of a primary drill member 14 and a secondary drill member 16. Adjacent and proximal to drill head 12 is drill body 18. Drill body 18 comprises at its distal end a housing 20. The proximal end of the drill body features a Hudson end 22 or a similar device that engages a drill chuck (not shown) to facilitate rotation of the drill. A device such as annular bearing 24 may assist in the engagement of the primary and secondary drill members 14, 16 within housing 20.

Figure 2A:
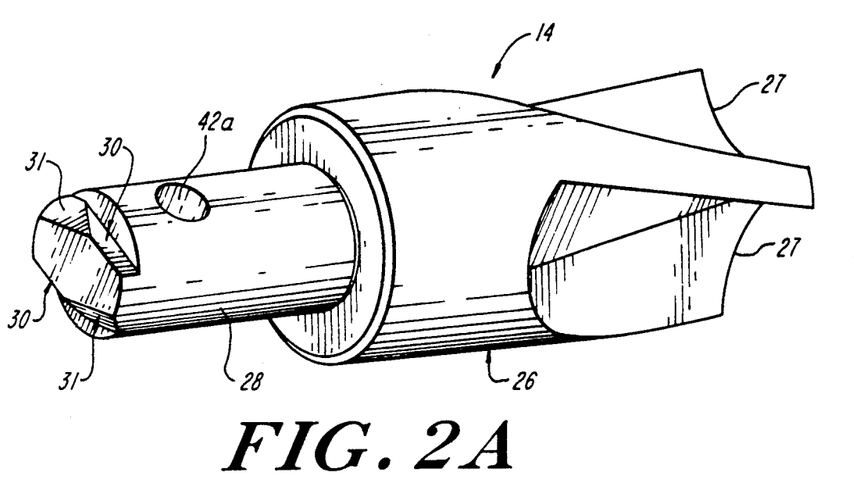
FIG. 2A is a view of the primary drill member of the drill assembly illustrated in FIG. 1.

As noted, drill head 22 comprises primary and secondary drill members 14, 16. Primary drill member 14, as shown in FIG. 2A, is an elongate member having a distal end 26 with cutting surfaces 28, and an elongate stem 28 at its proximal end. The proximal end of stem 28 features driver engaging surfaces 30 that are adapted to cooperate with the drive surfaces of a driver mechanism disposed within housing 20. Adjacent each driver engaging surface 30 is a ramped, non-engaging surface 31.

Figure 2B:
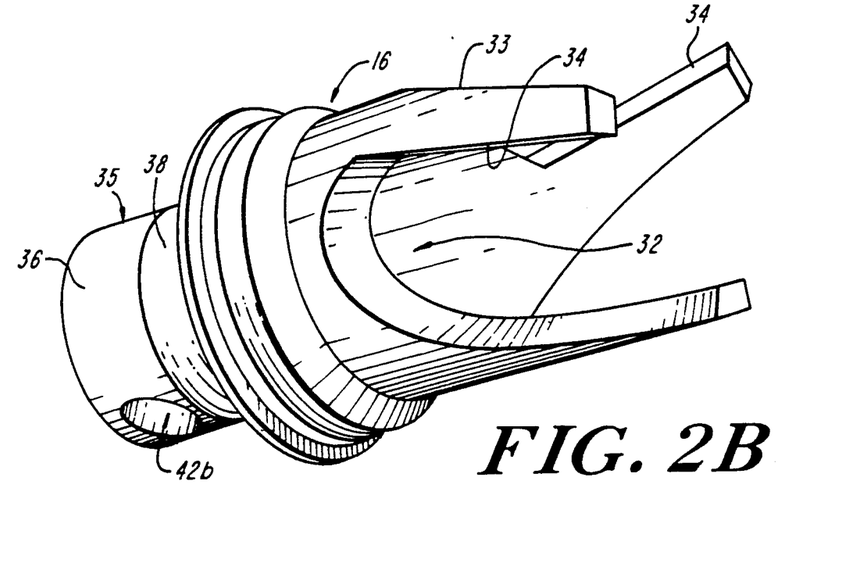
FIG. 2B is a view of the secondary drill member of the drill assembly illustrated in FIG. 1.

Secondary drill member 16 is cylindrical in shape and includes a central bore 32 that extends axially through member 16. The distal end 33 of member 16 includes cutting surfaces 34. The proximal end 35 of secondary drill member 16 includes a stem 36 having an annular groove 38.

Figure 1:
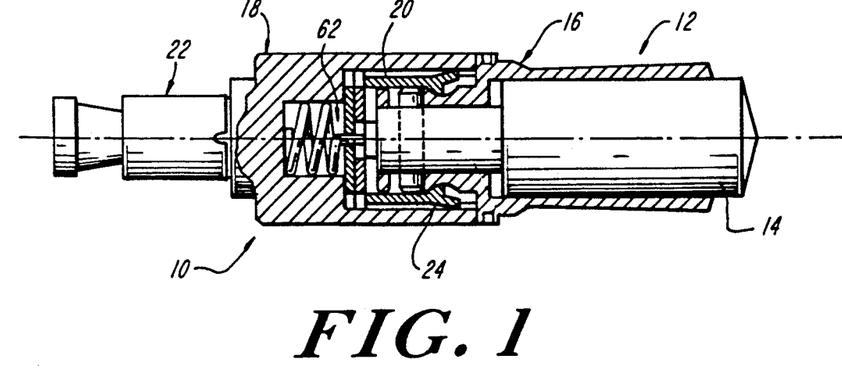
FIG. 1 is a view of a disposable drill assembly according to the present invention.
Figure 3:
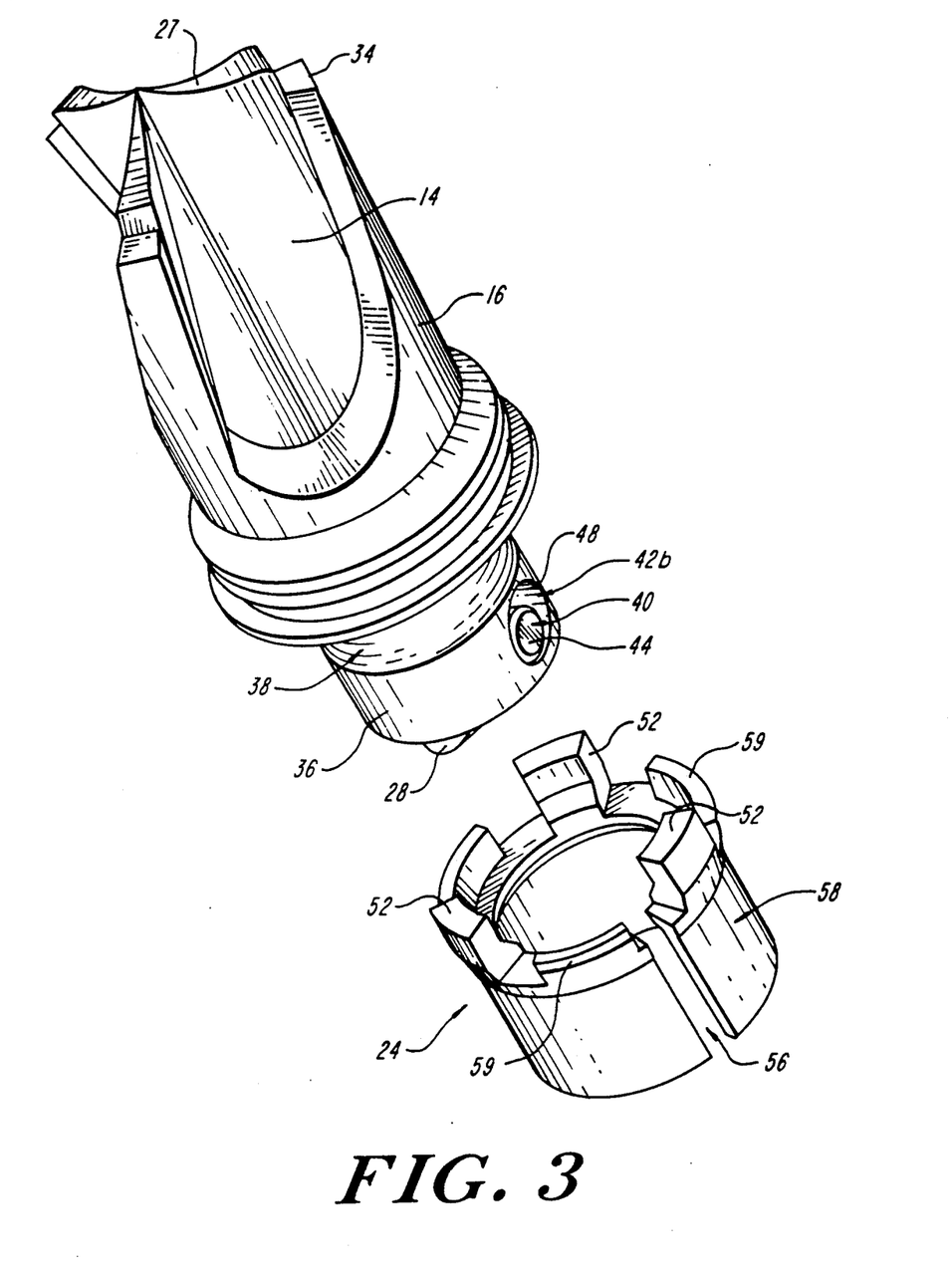
FIG. 3 is an exploded view illustrating the joined primary and secondary drill members and an annular bearing of the drill assembly of FIG. 1.

As illustrated in FIGS. 1 and 3, primary drill member 14 is disposed within the central bore 32 of secondary drill member 16. Preferably, the stem 28 of member 14 is slightly longer than the stem 36 of member 16 such that stem 28 protrudes from stem 36.

Assembled drill members 14, 16, as illustrated in FIGS. 1 and 3, preferably are coupled together such that rotation of primary drill member 14 facilitates rotation of secondary drill member 16 as well. Preferably, a coupling mechanism 40 joins together the two drill members 14, 16. Coupling mechanism 40 may comprise a bore 42 extending radially through each of stems 28, 36 and adapted to seat a dowel 44. Preferably the radial bore 42a disposed in stem 28 is of sufficient diameter to accommodate dowel 44 in a light press fit. Bore 42b disposed in stem 36 preferably is somewhat larger than dowel 44, particularly in the direction of the longitudinal axis of the drill member, in order to enable the primary drill member 14 to move axially with respect to secondary drill member 16. Preferably, bore 42b has a longitudinal dimension able to allow sufficient axial movement of stem 28 to enable engagement of driver engaging surfaces 30 with a driver.

Figure 3A:
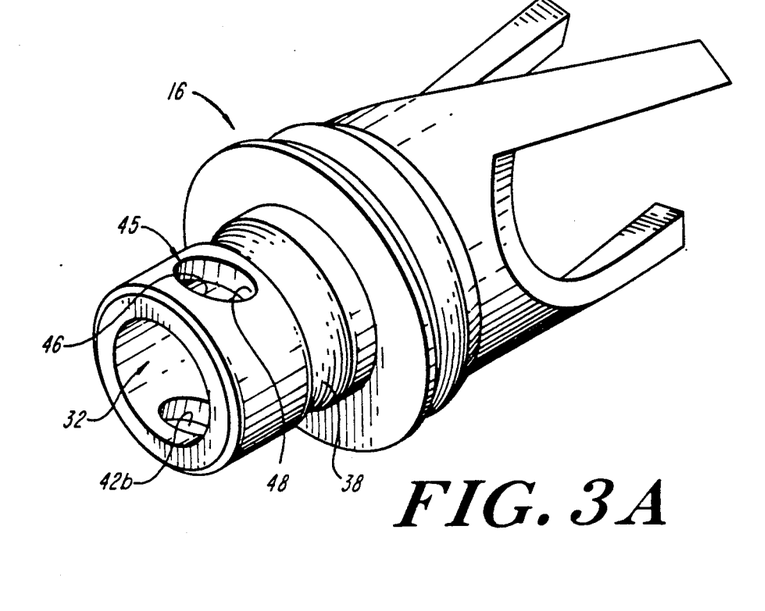
FIGS. 3A illustrates another view of the secondary drill member of FIG. 1.

In a preferred embodiment, radial bore 42b, disposed in stem 36, is essentially a triangular shaped cam 45. The cam can take a form similar to a right triangle, preferably having rounded corers. A ramped side 46 of cam 45 extends in the distal direction at about a 45° angle. Although 45° is the preferred angle, side 46 may be oriented at an angle of about 35° to 45°.

The angular orientation of side 46 of cam 45 assists in the disengagement of stem 28 of the primary drill member 14 from the drive mechanism disposed within housing 20. When an axial load is placed on the distal end 26 of primary drill member 14 the dowel 44 becomes positioned at the proximal end of side 46. As driver engagement occurs rotation of the primary and secondary drill members 14, 16 occurs and the dowel remains at the proximal end of side 46. The ramped side 46 assists in disengaging stem 28 of primary drill member 14 from the driver mechanism since, when the axial load drops below a certain desired threshold (e.g., below about 3 to 1 pounds), the torque of the rotating drill assembly is translated into axial motion in the direction away from the drive mechanism within housing 20.

Figure 4:
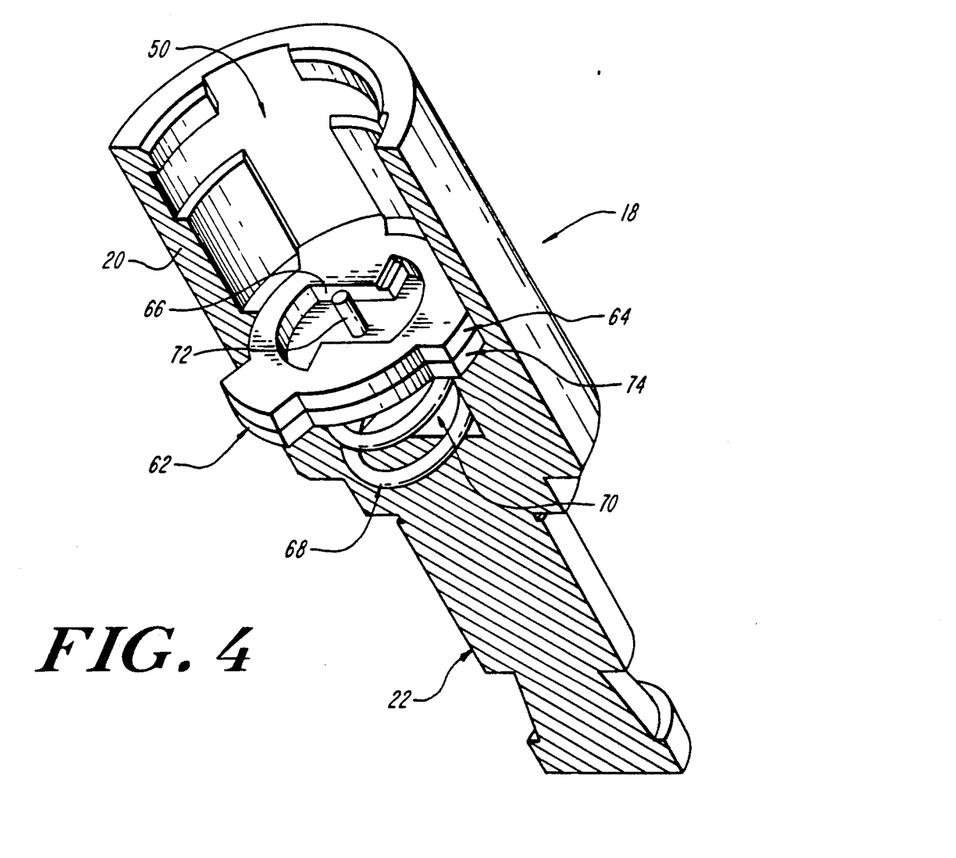
FIG. 4 is a cut-away view of a drill body useful with the drill assembly of FIG. 1.

The stems 28, 36 of drill members 14, 16 are disposed within housing 20 of drill body 18. The housing, as illustrated in FIG. 4, preferably comprises a bore 50 extending axially within a portion of drill body 18. The drill stems 28, 36 should be disposed within housing 20 such that the drill members 14, 16 are firmly engaged by drill body 18, but are still free to rotate independently of drill body 18 and housing 20.

In a preferred embodiment, an annular bearing 24 engages the drill stem 36 of drill member 16 in a clearance fit such that member 16 and bearing 24 are able to rotate independent of each other. Bearing 24, as illustrated in FIG. 3, preferably is of a substantially annular shape having a slot 56 disposed axially in one side of the bearing and extending over the length of the bearing. Slot 56 allows the bearing 24 to be expanded, enabling it to fit over stem 36 of member 36 of member 16. A distal end of bearing 24 preferably includes a plurality of extension arms 52. Extension arms 52 project, to some degree, toward the interior of bearing 24 enabling the arms 52 to engage an annular groove 38 in stem 36.

Bearing 24, when joined to stem 36, is adapted to be disposed within housing 20 in an interference fit such that the bearing is not able to rotate independently of drill body 18 and housing 20. Preferably, annular bearing 24 includes ribs 58 and extensions 59 that protrude outwardly from the outer surface of the bearing. Ribs 58 and extensions 59 are adapted to engage corresponding slots 60 within bore 50 of housing 20 to facilitate an interlocking fit of bearing 24 within bore 50. Preferably ribs 58 are aligned with extension arms 52 while extensions 59 are spaced between extension arms 52. As so constructed the drill head 12 is essentially permanently disposed on the drill body 18 within bore 50 of housing 20, and absent destruction of a portion of the housing, it is generally not possible to separate the drill head from the drill body. This is advantageous from a safety standpoint in that it ensures that the drill assembly 10 will indeed be disposed of after use since it is not possible to disassemble and reassemble the drill assembly. Also, since it is not possible to clean the drill assembly after use, there will be no incentive to reuse the drill.

In one embodiment it is possible to include an indicator device (not shown) such as a polymeric ring at some location on the drill assembly, and preferably on stem 36. Such an indicator device preferably has a melting temperature below that at which serialization generally occurs, enabling it to provide an indicator that reveals whether reuse has been attempted. Acrylonitrile butadiene styrene is one example of a polymeric material suitable for use as an indicator ring.

Assembly 10 includes a clutch mechanism 62 to enable rotation of the drill head 12 to take place only upon the presence of a sufficient axial load on primary drill member 14. A clutch mechanism of the type known in the art can be used with the drill assembly 10 of the invention.

In a preferred embodiment, however, clutch mechanism 62 is disposed at the bottom of housing 20, and includes a driver 64 having substantially vertical (i.e., axially oriented) drive surfaces 66, and a spring 68, or similar compression device, for biasing the driver engaging surfaces 30 of stem 28 away from vertical driver surfaces 66. In a preferred embodiment, illustrated in FIGS. 1 and 4, the spring 68. is disposed within an axial bore 70 disposed at the bottom of housing 20. The spring 68 preferably includes a vertical protrusion or plunger 72 that extends into bore 50 of housing 20. Preferably, the spring 72 is maintained in place by a washer device 74 that mounts at the bottom of bore 50. Washer 74 preferably includes a central aperture 76 for receiving plunger 72. In a preferred embodiment, a drive washer 78, having substantially vertical drive surfaces 66, is disposed above washer 74.

As illustrated in FIGS. 5A through 5C and FIG. 6, the washer 74 and drive washer 78 are generally circular in shape, and each have extension arms 80 for engaging slots 60 in housing 20 to insure that washers 74, 78 remain firmly affixed within the housing and rotate only with the housing. Preferably, arms 80 engage slots 60 within bore 50 of the housing 20.

Figure 5A:
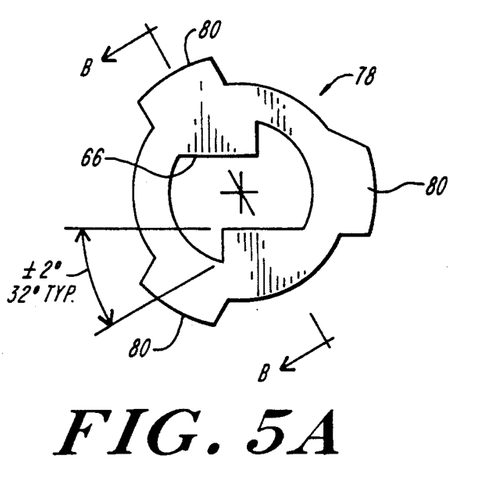
FIG. 5A is a view of a driver useful with the drill assembly of the invention.
Figure 5B:
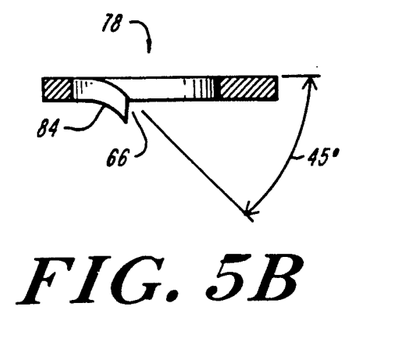
FIG. 5B is a sectional view of the driver of FIG. 5A, along lines B—B.
Figures 5C, 6:
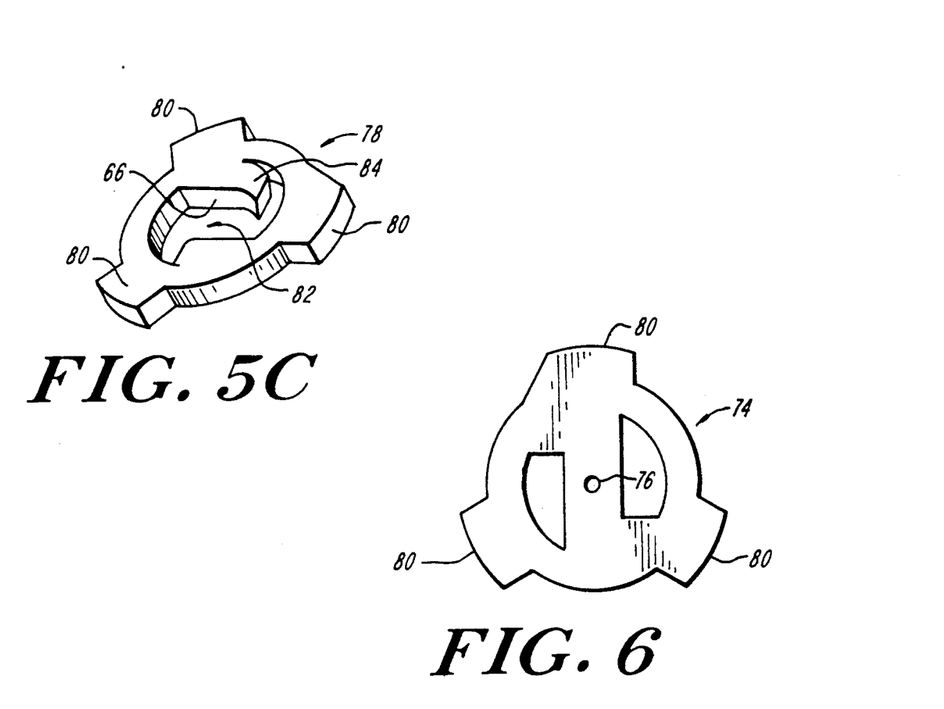
FIG. 5C is another view of the driver shown in FIG. 5A.
FIG. 6 is a view of a washer insert useful in the drill assembly of the present invention, in conjunction with the driver of FIGS. 5A-5C.

The drive washer 78 preferably is constructed so as to facilitate only clockwise rotation of drill head 12. Accordingly, as shown in FIGS. 4, 5B and 5C, the drive surfaces 66 of drive washer 78 are substantially vertical. When the biasing force of spring 68 is overcome by an axial load placed on primary drill member 14, the driver engaging surfaces 30 on stem 28 extend within an aperture 82 within drive washer 78, enabling the substantially vertical drive surfaces 66 to contact the driver engaging surfaces 30 to facilitate clockwise rotation of drill head 12. Any counterclockwise rotation of drive washer 78 will not result in counterclockwise rotation of drill head 12. A ramped surface 84 adjacent each drive surface 66 on drive washer 78 prevents any counterclockwise rotation of drill head 12. As the housing 20 and drive washer 78 rotate in a counterclockwise direction the ramped surface 84 contacts the non-engaging surface 31 of stem 28 causing the non-engaging surfaces 31 to ride up the ramped surface 84 without effecting rotation of drill head 12. The surface 84 is inclined at an angle of ranging from about 45° to 55°, but preferably is about 45°.

As illustrated in FIG. 5B, the vertical drive surfaces 66 of drive washer 78 preferably are formed on a downwardly projecting portion of the drive washer 78. Similarly, ramped surfaces 84 are formed on a downwardly projecting portion of drive washer 78.

In another embodiment, illustrated in FIGS. 7 through 10B, the invention comprises a drill assembly 86, at least the drill body of which is reusable. Drill assembly 86 comprises a drill head 88, at a distal portion thereof, having a primary drill member 14 and a secondary drill member 16. The proximal end of the drill assembly comprises a drill body 90. As noted, drill assembly 86 is capable of reuse, but in a preferred embodiment the drill head 88 is disposable while only the drill body 90 is reuseable.

The drill head 88 used with the embodiment of this invention may be similar or identical to that described above with respect to the disposable embodiment. Accordingly, reference numerals used in FIGS. 7 through 9, and in the description below, correspond to like reference numerals used to identify various portions of the drill head 12 discussed above.

Figure 7:
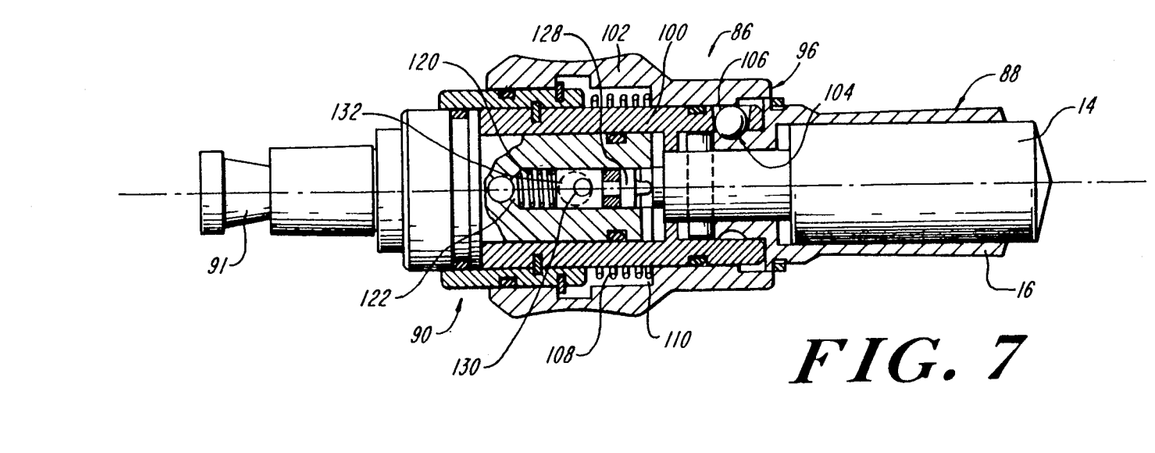
FIG. 7 is a sectional view of a reusable drill assembly of the present invention.
Figure 8:
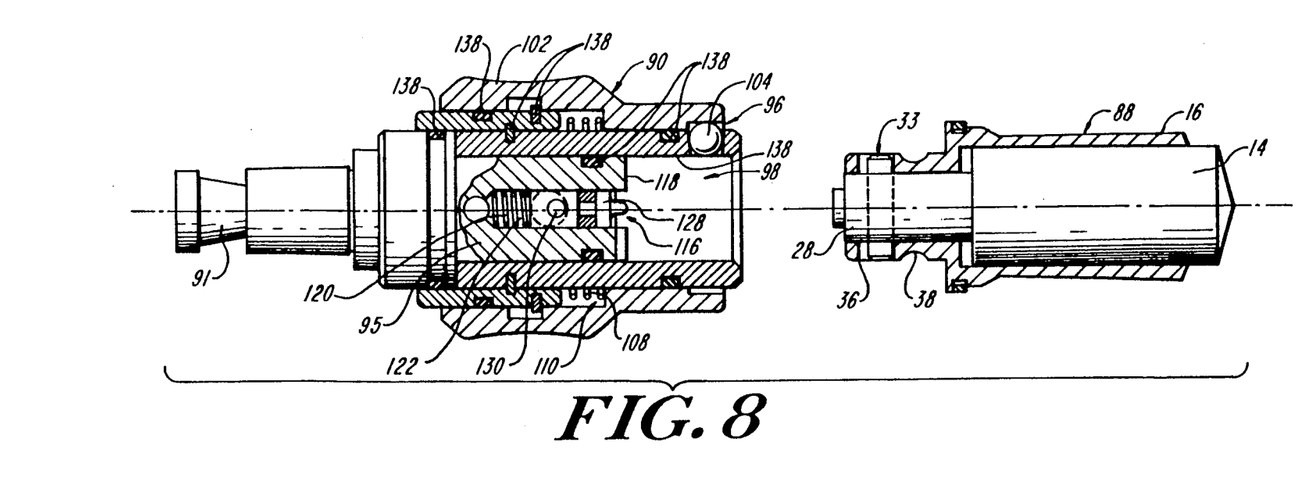
FIG. 8 is an exploded view of the drill assembly of FIG. 7, showing the drill head detached from the drill body.
Figure 9:
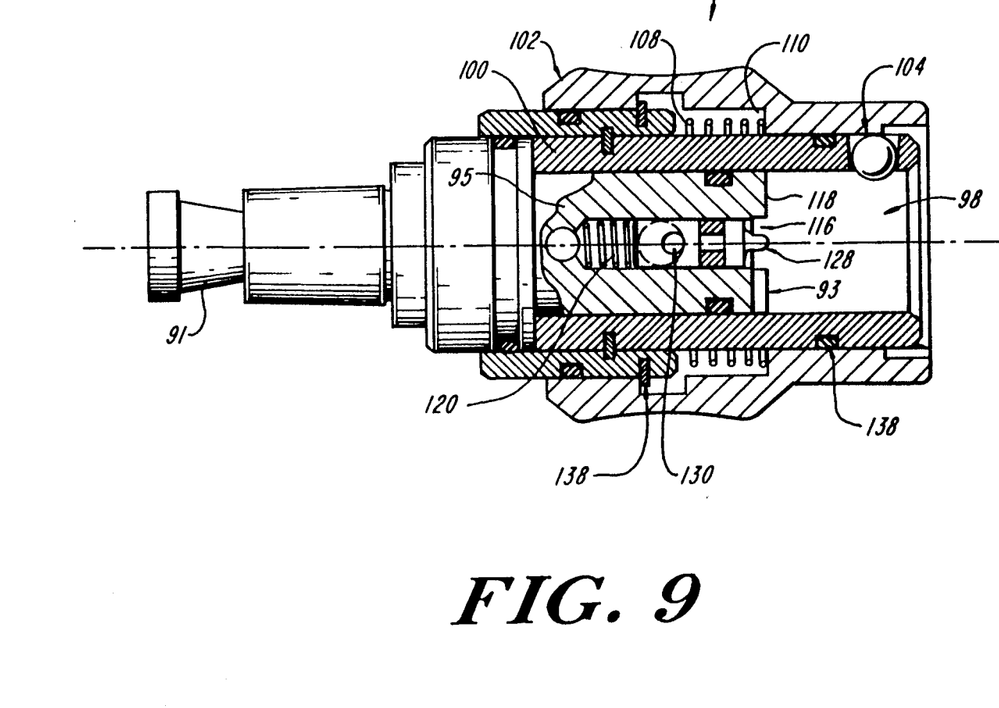
FIG. 9 is a sectional view of the drill body shown in FIGS. 7 and 8.

The reusable drill body 88 comprises a drill housing 96 having a cylindrical socket 9 8 disposed therein. A proximal portion of drill body 88 includes a Hudson end 91 or similar device for engaging a drill chuck (not shown). Drill body 88 also includes an elongate member 93 integral with and distal to end 91. The distal end 95 of member 93 preferably forms the base of socket 98. The socket 98 is defined by an inner sleeve 100, disposed on member 93, and is adapted to receive the elongate stems 28, 36 of drill head 88. A retractable outer sleeve 102 is disposed over the inner sleeve 100. Preferably, the outer sleeve 102 is biased to a non-retracted position, as shown in FIG. 7, by spring 108, or by a similar biasing device that engages a shoulder 110 on an interior portion of outer sleeve 102. Inner sleeve 100 includes an engagement bearing 104 that protrudes through an aperture 106, preferably located toward the distal end of the socket 98. The engagement bearing 104 is disposed within the inner sleeve 102 such that it is capable of radial displacement. Thus, when the outer sleeve is in the non-retracted position, as in FIG. 7, bearing 104 is forced into an interior portion of the socket 98. When outer sleeve 102 is fully retracted, as shown in FIG. 8, bearing 104 is free to move outwardly so that it does not occupy any portion of the interior of socket 98. Preferably, a distal end 33 of outer sleeve 102 has an annular groove 38 that is engaged by bearing 104 when it is forced into the interior of socket 98 by the force of outer sleeve 102. Bearing 104 has a diameter of about 1.5 mm to 4.7 mm.

The proximal end of drill head 12 comprises the stems 28, 36 of the primary and secondary drill members 14, 16. The diameter of socket 98 preferably is slightly greater than the diameter of stem 36, thus allowing stem 36 to be disposed within socket 98 in a light press fit that enables rotation of drill head 12 independent of drill body 90 and a driver mechanism disposed therein.

As shown in FIG. 8, the outer sleeve 102 is fully retracted, enabling bearing 104 to be displaced from the interior of socket 98. This enables stems 28, 36 of drill head 12 to be inserted into socket 98. Once the outer sleeve 102 is allowed to return to its natural, forward position bearing 104 is forced into the interior of socket 98 and engages annular groove 38 on stem 36 to secure the drill head 88 to the drill body 90.

The reusable drill assembly 86 includes a clutch mechanism 116 disposed within drill body 90 to facilitate rotation of the drill head 12 only when the primary drill member 14 is subjected to a sufficient axial load. Preferably, the clutch mechanism 116 facilitates only clockwise rotation of the drill head 12. The clutch mechanism used with reusable drill assembly 86 may be similar or identical to that described above with respect to the disposable drill assembly 10. In a preferred embodiment, however, the clutch mechanism 116 is somewhat different in construction in that a driver 124 and its drive surfaces 126 are integral with a bottom portion 118 of socket 98, formed by distal end 95 of member 93. This construction feature may provide a more durable drill body having a longer useful life.

As illustrated in FIGS. 7 through 10B, clutch mechanism 116 includes a spring 120, or similar compression means, that is disposed within a bore 122 formed within member 93. The spring 120 is adapted to apply a force against a plunger device 128 which extends into the socket 98. The plunger 128 can be maintained within the bore 122 by a motion limiting device. In a preferred embodiment, this device is a dowel pin 130 extending radially through elongate member 93 and plunger 128 within radial bore 132 formed in elongate member 93. Preferably, dowel pin 130 has a smaller diameter than the radial bore 132 and a corresponding bore (not shown) formed in plunger 128 such that the plunger 128 has limited axial motion. The spring 120 and plunger 128 combine to bias the stem of primary drill member 92 away from the driver 124 and its associated drive surfaces.

Figure 10A:
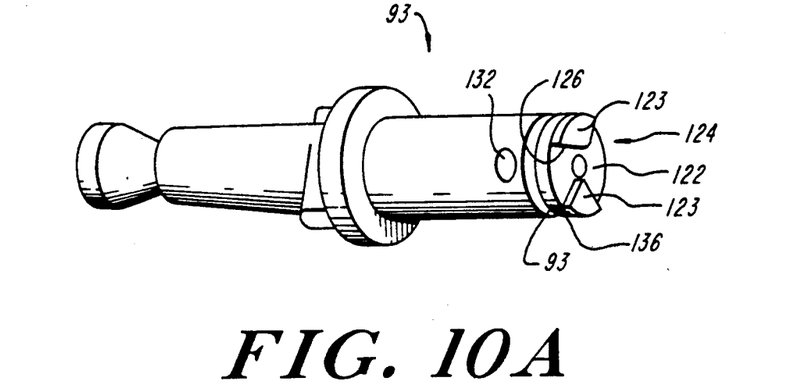
FIG. 10A is a side view of a member that forms a proximal portion of the drill body of FIG. 7.
Figure 10B:
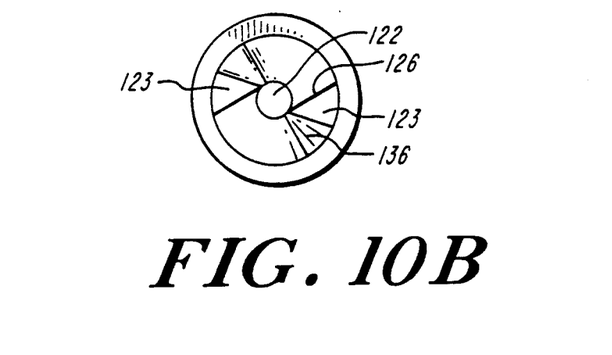
FIG. 10B is a distal end view of the member of FIG. 10A.

The driver 124, as illustrated in FIGS. 10a and 10b, is disposed on a distal end 95 of elongate member 93. Preferably, driver 124 has substantially vertical drive surfaces 126 that project from distal end 95 of member 93. The drive surfaces 126 preferably are constructed so as to facilitate only clockwise rotation of the primary and secondary drill members 92, 94. Preferably, drive surfaces 126 are formed on opposed, substantially triangular projections 123. Adjacent each drive surface 126 is a ramped non-drive surface 136. Ramped non-drive surface 136 preferably is disposed at a radius of about 0.060 to 0.080 such that upon counterclockwise rotation of drill body 90, ramped surface 136 does not engage surfaces on the stem 28 of primary drill member 92 and thus prevents counterclockwise rotation of drill head 88. When the biasing force of the spring 120 is overcome by axial load against the plunger 128 by the primary drill member 14, the driver engaging surfaces 30 on stem 28 extend within a space between projections 123. This enables the substantially vertical drive surfaces 126 to contact the driver engaging surfaces 30 to facilitate clockwise rotation of the drill head 12.

The reusable drill assembly 86 preferably is sealed at appropriate points along the drill assembly to ensure sterility of the device. Such sealing allows the drill assembly 86 to be sterilized after use without the need for disassembly. In a preferred embodiment, the assembly is sealed by using high temperature resistant O-rings 138 placed at locations that will be appreciated by those having ordinary skill in the art.

In addition, a plunger O-ring 146 preferably is used to provide a seal about the plunger 128 without reducing its mobility. The plunger O-ring 146 is typically placed at a distal portion of the plunger 128 so that the axial displacement of the plunger does not allow contamination of the radial bore 132 or spring 120.

The drill assembly of the present invention may be constructed of a variety of materials that are customarily used in the manufacture of surgical drills. One having ordinary skill in the art will readily appreciate the materials that most desirably may be used to construct the present drill assemblies. In a preferred embodiment, however, the disposable drill body 18 and annular bearing 24 may be constructed of polymeric materials while reusable drill body 90 can be constructed from polymers. Stainless steel is, however, a preferred material.

The invention may be embodied in other specific forms without departing from the spirit or other characteristics thereof. The present embodiments are, therefore, to be considered in all respects as illustrative and not restrictive. The scope of the invention is indicated by the appended claims rather than by the foregoing description, and all changes which come within the meaning and range of equivalency of the claims are, therefore, intended to be embraced therein.

What is claimed is:

1. A drill apparatus for penetrating bone, comprising
   a generally cylindrical primary drill member having cutting surfaces at a distal end thereof and an elongate stem at a proximal end thereof, the stem having at least one driver engaging surface at its proximal end;
   a generally cylindrical secondary drill member having cutting surfaces at a distal end thereof and a stem at a proximal end thereof, the secondary drill member having an axial bore extending therethrough for receiving the primary drill member in a clearance fit such that at least a portion of the proximal end of the primary drill member stem is able to protrude from the proximal end of the bore in the secondary drill member;

coupling means for joining the primary and secondary drill members to facilitate the rotation of the secondary drill member upon rotation of the primary drill member;

a drill body member for receiving proximal portions of the primary and secondary drill members, the drill body member having at a distal end thereof a cylindrical portion with a first axial bore extending therein for a distance less than the length of the drill body member, and having an elongate stem extending proximally from the cylindrical portion for insertion into a drill chuck; and a clutch mechanism having a driver means for facilitating clockwise rotation of the primary drill member, the driver means being disposed at a bottom portion of the first axial bore of the drill body member and having at least one substantially vertical drive surface for engaging the driver engaging surface of the primary drill member stem upon clockwise rotation of the driver means and an angled non-drive surface adjacent the drive surface that is unable to engage the driver engaging surface of the primary drill member stem upon counterclockwise rotation of the driver means; and compression means for biasing the stem of the primary drill member away from the driver means to prevent rotation of the primary dill member absent an axial load on the primary drill member able to overcome the biasing force of the compression means.

2. The apparatus of claim 1 further comprising bearing means, mountable upon the stem of the secondary drill member, for securing the primary and secondary drill members to the drill body member through a clearance fit, the bearing means being disposed within the first axial bore of the drill body member in an interference fit and enabling the drill members to rotate independently of the drill body member.

3. The apparatus of claim 2 wherein the bearing means is generally annular in shape, having a central opening therein to enable mounting of the bearing means over the stem of the secondary drill member while allowing free rotation of the primary and secondary drill members relative to the bearing means, the bearing means further comprising radial projections that bear on inner walls of the first axial bore to facilitate an interference fit between the bearing means and inner walls of the first axial bore.

4. The apparatus of claim 1 wherein the driver means comprises a first washer-like insert disposed within the first axial bore, at a bottom portion thereof.

5. The apparatus of claim 4 wherein the drive surface is formed on a downwardly projecting structure of the first washer-like insert.

6. The apparatus of claim 5 wherein the driver means further comprises a second washer-like insert having a centrally disposed aperture therein and at least one non-centrally disposed aperture that accommodates the downwardly projecting structure of the first washer-like insert, the second washer-like insert adapted to be disposed within the first axial bore beneath the first washer-like insert.

7. The apparatus of claim 1 wherein the drill body member further comprises a second axial bore for receiving the compression means, the second axial bore being concentric with the first axial bore and of lesser diameter than the first axial bore and being disposed at the bottom of the first axial bore.

8. The apparatus of claim 7 wherein the compression means comprises a spring having an extended, vertical plunger portion that contacts and biases the stem of the primary drill member out of engagement with the drive surface of the driver means.

9. The apparatus of claim 1 wherein the coupling means comprises a hole extending radially through the elongate stem of the primary drill member;

a dowel having a length greater than the diameter of the elongate stem of the primary drill member for insertion within the hole; and two opposed orifices disposed in the stem of the secondary drill member, the orifices for receiving and engaging portions of the pin that extend beyond the diameter of the elongate stem of the primary drill member.

10. The apparatus of claim 9 wherein the orifices disposed in the stem of the secondary drill member are substantially in the shape of a right triangle having first and second sides respectively extending parallel and transverse to the longitudinal axis of the stem and having a third side inclined at an angle of approximately 45° with respect to the first and second sides.

11. The apparatus of claim 10 wherein the side of the triangular shaped orifice extending parallel to the longitudinal axis is about 2.5 to 4.0 mm in length.

12. The apparatus of claim 1 wherein the stem of the primary drill member requires axial displacement of about 0.5 to 2.5 mm to enable the driver engaging surfaces to engage the drive surfaces of the driver.

13. The apparatus of claim 12 wherein the axial load applied to the primary drill member must exceed about 3 to 10 pounds to cause axial displacement of the stem of the primary drill member.

* * * * *